United States Patent [19]
Leong et al.

[11] Patent Number: 5,950,234
[45] Date of Patent: Sep. 14, 1999

[54] COOLING PACK HEAD COVERING

[76] Inventors: Randy Leong, 705 Oceanhill Dr., Huntington Beach, Calif. 92648; Penelope Kittredge, 13528 Bassett St., Van Nuys, Calif. 91405

[21] Appl. No.: 08/825,606

[22] Filed: Mar. 31, 1997

[51] Int. Cl.⁶ .................................................. A42B 1/00
[52] U.S. Cl. ..................... 2/7; 2/171.2; 607/110
[58] Field of Search ................ 2/7, 171.2; 607/110, 607/109

[56] References Cited

U.S. PATENT DOCUMENTS

| | | | |
|---|---|---|---|
| 2,158,571 | 5/1939 | Culp | 2/7 |
| 5,305,470 | 4/1994 | McKay | 2/7 |
| 5,469,579 | 11/1995 | Tremblay et al. | 2/7 |

*Primary Examiner*—Diana L. Oleksa
*Attorney, Agent, or Firm*—Dennis W. Beech

[57] ABSTRACT

The cooling pack is a container having a cooling substance contained within it. The cooling pack is generally constructed such that it can be formed in a bowl shape to cover the scalp portion of the users head. By covering the scalp with a cooling pack the lose of hair is minimized during medical treatments such as chemotherapy. The cooling pack may also be used with head wear such as hats, helmets and the like. In addition a head band may have a cooling pack to be worn over the eyebrows.

1 Claim, 1 Drawing Sheet

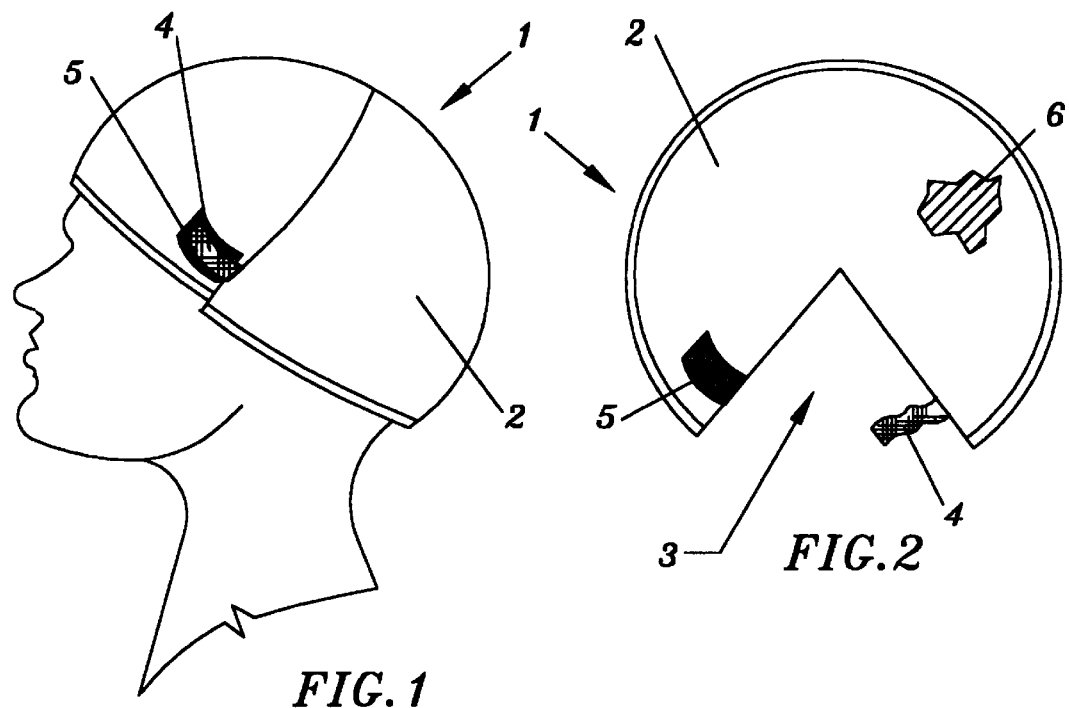
FIG.1
FIG.2
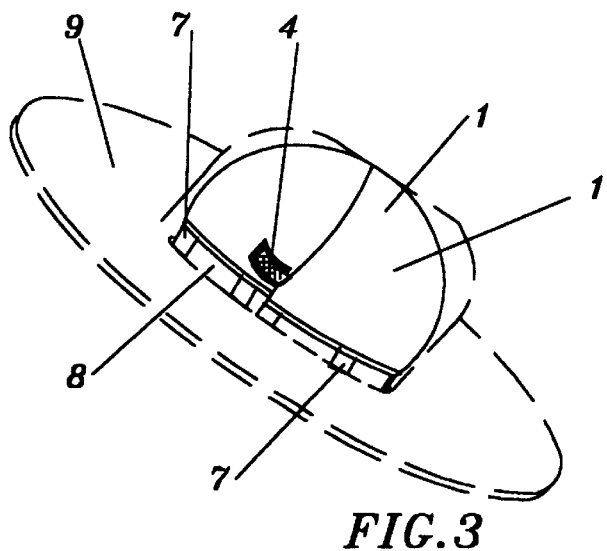
FIG.3
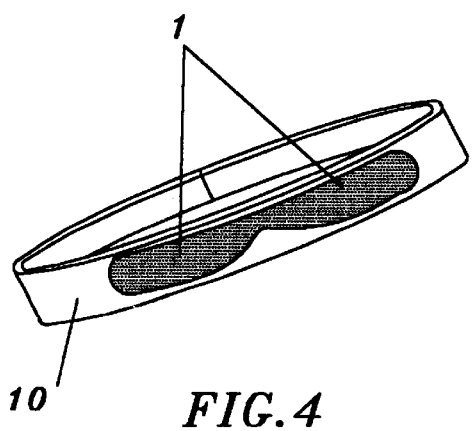
FIG.4

COOLING PACK HEAD COVERING

BACKGROUND OF THE INVENTION

1. Field of the Invention

This invention relates to human head coverings for medical treatment. The new device provides a head cover which has a cold substance contained therein to cool the scalp.

2. Description of Related Art

There are currently in use various ice pack, cold pack and chemical cold pack devices which are placed on areas of the human body to reduce the temperature of the area to which applied. These devices are usually constructed of a plastic container or pack which contains the cooling material. The most basic of these is a bag with ice in it.

More sophisticated cooling devices usually involve the use of a plastic container having a chemical substance which may be cooled and then used when required. Another version of this type of device is the chemical cold pack in which the chemicals in the container become cold when they are mixed together by the breaking of a barrier separating them. All of these devices are normally packs of standard geometrical shape such as rectangular. Some are constructed in a cylindrical shape to wrap around an arm or leg.

The present invention provides a cold pack which fits on the scalp portion of the head. The pack is shaped to cover the scalp in order to reduce the temperature as for example when a person is undergoing chemotherapy treatment. By cooling the scalp in conjunction with such treatment loss of hair may be minimized.

SUMMARY OF THE INVENTION

A primary objective of the present invention is to provide a cooling pack for covering the scalp of a persons head. Another object is provide a cooling pack which may be worn with other head coverings such as hats, helmets, caps and the like. A further object is to provide a cooling pack for covering the eyebrow area of the head.

In accordance with the description presented herein, other objectives of this invention will become apparent when the description and drawings are reviewed.

BRIEF DESCRIPTION OF THE DRAWING

FIG. 1 illustrates a side elevation view of the cooling pack on a persons scalp.

FIG. 2 illustrates a plan view of the cooling pack spread flat.

FIG. 3 illustrates a perspective view of the cooling pack adopted to fit in a hat.

FIG. 4 illustrates a perspective view of a cooling pack for covering a persons eyebrows.

DESCRIPTION OF THE PREFERRED EMBODIMENT

The cooling pack is a container normally constructed of plastic having a cooling substance contained therein. The container shape is designed to fit over the scalp of a person. The cooling substance may be a material designed to be cooled in a refrigeration unit and then used when needed. Another method is to use separate substances that when mixed become cool in the container. The cooling pack may also be in the shape of a head band with the cooling substance applied over the eyebrows. The use of the cooling pack reduces the temperature in the area of application to minimize hair loss when chemotherapy treatment is undertaken.

Referring to FIGS. 1 through 3, the cooling pack (1) is a generally circular shaped container (2) with a "V" shaped notch (3) formed therein. There is a strap (4) having a hook and loop fastener (5) to attach to the body of the container (2) to hold the container (2) in the particular shape necessary to fit the users scalp. The container (2) has a cooling substance (6) such as compounds which may be cooled in a refrigeration unit or chemicals which when mixed become cool for a period of time. Such mixing chemicals are commonly used wherein a barrier in the pack is broken to cause the chemical reaction when the cooling application is required.

The cooling pack (1) is normally worn as prescribed by a physician who is in charge of the individuals medical treatment. It has been found by experiment that wearing a cooling pack (1) for a few hours in conjunction with and after chemotherapy minimizes the loss of scalp hair.

In FIG. 3 the cooling pack (1) has been constructed with tabs (7) for fitting in the hat band (8) of a hat (9). This configuration provides the user with a convenient means to wear the cooling pack (1) and to hide its use if desired. Obviously other configurations may be used such as in a helmet, cap or the like headware.

While a generally bowl shaped cooling pack (1) is described in the preferred embodiment, other configurations are possible. For example, if a football helmet were used the cooling pack (1) might be formed in multiple parts to fit in the helmet. So long as the scalp is cooled to a temperature to minimize hair loss, the cooling pack (1) may take a variety of shapes. If a person has particularly long hair the cooling pack (1) may have a wrap to engage the longer strands of hair.

Referring to FIG. 4, a further variation of the cooling pack (1) is illustrated wherein the container (2) is formed in a head band (10). In this embodiment the cooling pack (1) may be worn over the users eyebrows to cool the area to minimize hair loss.

I claim:

1. A device for cooling a user's scalp comprising:

a flexible container of generally flat circular shape having a cooling substance contained therein to form a cooling pack;

the flexible container having a notch defined therein which allows the flexible container to be wrapped over and around a user's scalp;

a means for retaining the flexible container in the wrapped position; and the flexible container adapted to cover the entire scalp of a user.

* * * * *